US00PP15963P2

(12) United States Plant Patent
Tupy et al.

(10) Patent No.: US PP15,963 P2
(45) Date of Patent: Sep. 13, 2005

(54) APPLE TREE NAMED 'UEB 3264/2'

(50) Latin Name: *Malus Mill.*
Varietal Denomination: UEB 3264/2

(75) Inventors: Jaroslav Tupy, Praha (CZ); Otto Louda, Praha (CZ); Jan Zima, Turnov (CZ)

(73) Assignee: Institute of Experimental Botany (CZ)

( * ) Notice: Subject to any disclaimer, the term of this patent is extended or adjusted under 35 U.S.C. 154(b) by 4 days.

(21) Appl. No.: 10/862,259

(22) Filed: Jun. 7, 2004

(51) Int. Cl.[7] ..... A01H 5/00
(52) U.S. Cl. ..... Plt./172
(58) Field of Search ..... Plt./172

*Primary Examiner*—Anne Marie Grunberg
(74) *Attorney, Agent, or Firm*—The Webb Law Firm

(57) ABSTRACT

A new and distinct *Malus Mill.* plant that produces apples having a pleasant aroma and sweet taste suitable for use as a dessert fruit.

4 Drawing Sheets

Botanical classification: *Malus Mill.*
Varietal denomination: 'UEB 3264/2'.

BACKGROUND OF THE INVENTION

The present invention comprises a new and distinct cultivar of apple tree botanically classified as *Malus Mill.* and known by the varietal name 'UEB 3264/2', also known as 'Opal' in the Czech Republic. The new variety was discovered in the fall of 1999 in The Czech Republic. The new variety is the result of a planned breeding program between unpatented female parent 'Golden Delicious' and unpatented male parent 'Topaz'. The purpose of the breeding program was to find a new cultivar with high disease resistance, high yield, and excellent fruit quality. The new variety exhibits similar fruit taste, fruit shape and yellow ground color of fruits to 'Golden Delicious', but exhibits a shorter fruit stem, a broader eye basin of the fruit, the presence of $V_f$-resistance against scab, and longer fruit storage capacity. The new variety exhibits similar $V_f$-resistance against scab and russeting in the fruit stem cavity to 'Topaz'. The new variety differs from 'Topaz' in the following ways. The fruit shape of the new variety is globose to globose-conical whereas 'Topaz' is flat globose. The fruit overcolor of the new variety is absent or present as a slight orange blush whereas in 'Topaz' the overcolor is orange-red to dark red as stripes and is present on 75% of the fruit surface. In the new variety, the greasiness of the fruit skin after storage is absent or very weak, whereas in 'Topaz' it is present. The new variety also has a sweet fruit taste whereas 'Topaz' is rather tart.

The following characteristics distinguish the new variety from other *Malus Mill.* varieties:

Late, dessert-type, diploid variety

Trees are of medium vigor with an upright to spreading habit

Fruit shape is globose, sligtly conical (less conical than 'Golden Delicious'

Stalk is medium long and medium thick

Russeting is present in the stem cavity

Ground color of the fruit skin is yellow

Overcolor is either absent or a slight orange blush

Fruit flesh is firm, juicy; with a sweet aromatic flavor

Keeping quality of the fruits is very good $V_f$-resistance against scab is present The new variety has been trial and field tested and has been found to retain its distinctive characteristics and remain true to type through successive propagations. The new variety has not been publicly available or offered for sale anywhere in the world before the filing date of the present application. The new variety is the subject of Plant Breeders' Rights Application Number 1309/MAL08139, filed Nov. 13, 2001, in The Czech Republic.

DESCRIPTION OF THE DRAWINGS

The accompanying photographic drawings illustrate the new cultivar, with the color being as nearly true as is possible with color illustrations of this type.

DESCRIPTION OF THE PLANT

Figure 1:
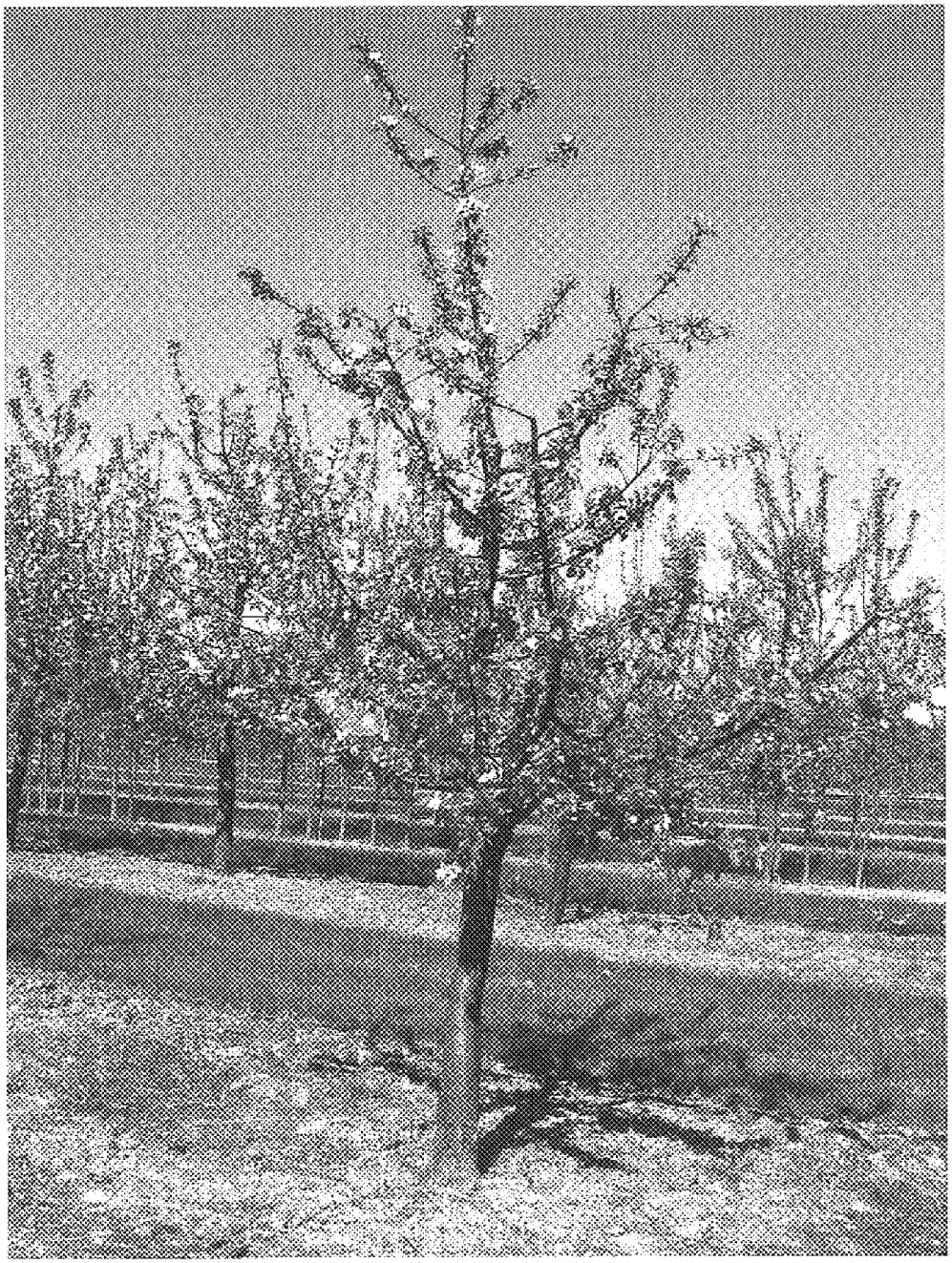
FIG. 1 shows the new variety grafted on a seedling.
Figure 2:
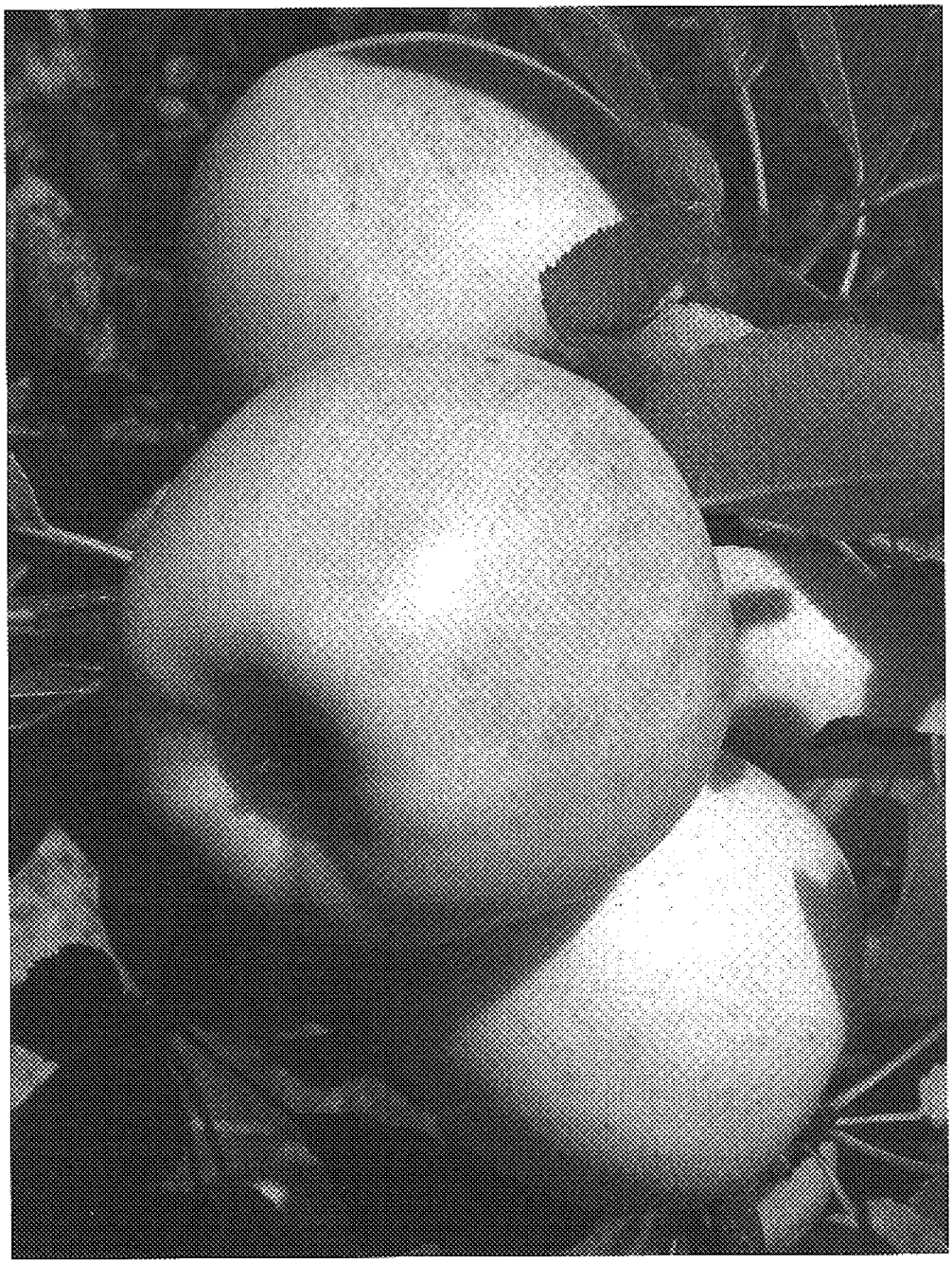
FIG. 2 shows a close-up view of the fruits of the new variety at maturity.
Figure 3:
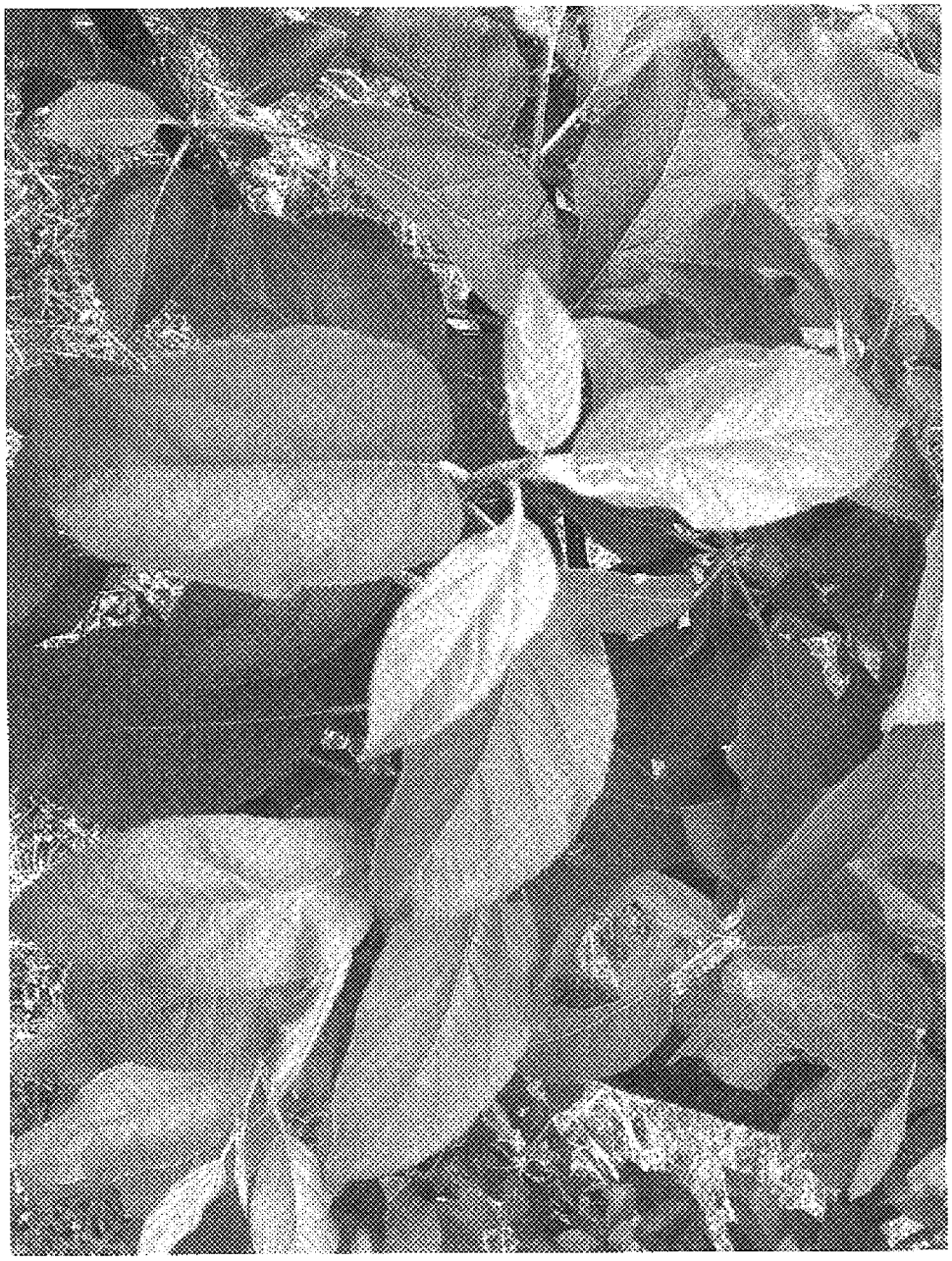
FIG. 3 shows the leaves of the new variety.
Figure 4:
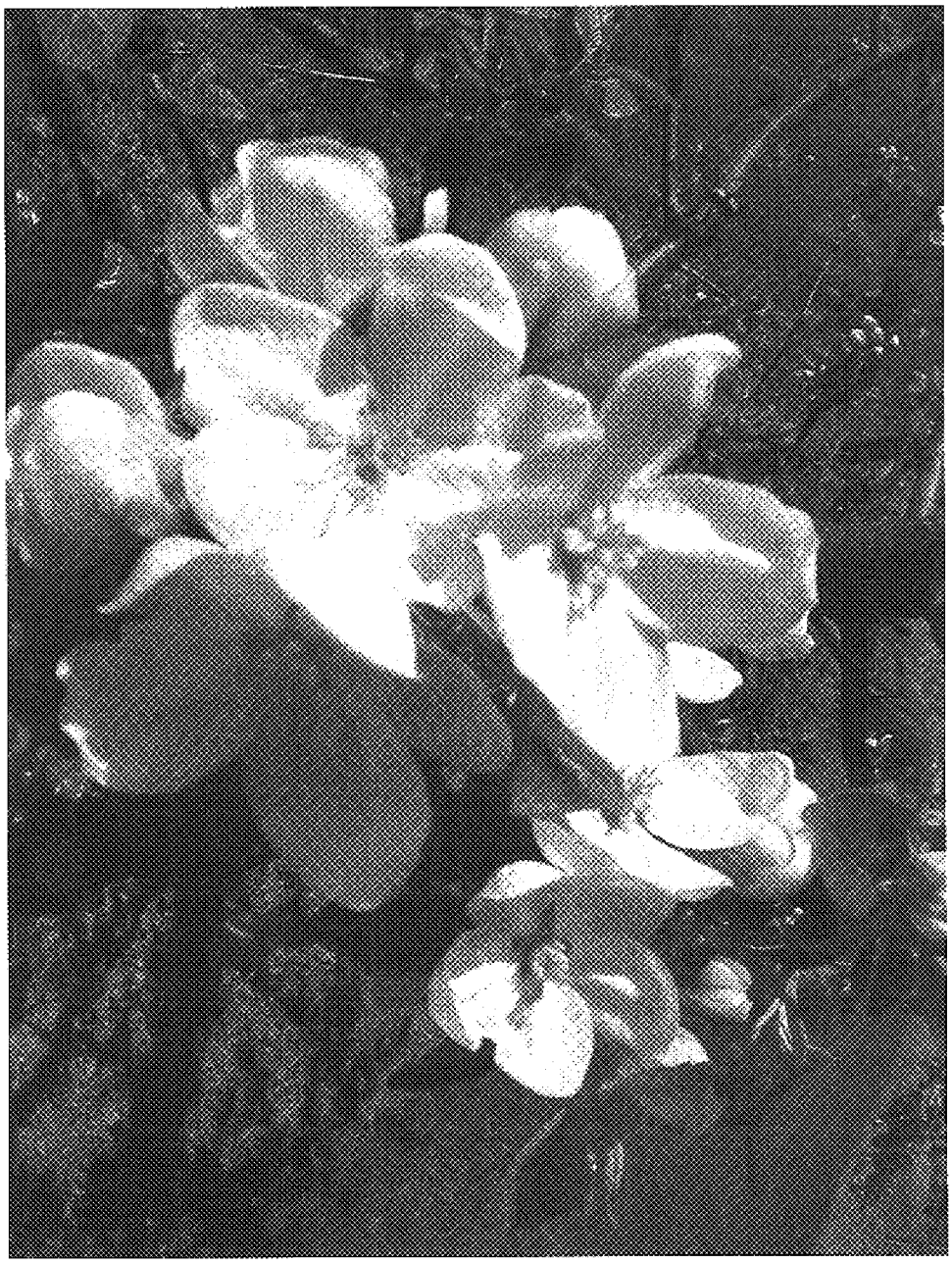
FIG. 4 shows the blossoms of the new variety.

The following detailed description sets forth the characteristics of the new cultivar. The data which defines these characteristics were collected by asexual reproductions by budding and grafting on apple tree rootstocks, including mostly 'M-9' rootstock, first carried out in The Czech Republic in the spring of 2000. The new variety was grown in a field under natural conditions with fertilization in kg/ha/year of N 55, P 25, K 60, Ca 55, and Mg 5. The color readings were taken in natural daylight. Color references are primarily to The R.H.S. Colour Chart of The Royal Horticultural Society of London.

TREE

Age: 9 years old.
Size: At crown — 3.0 m high, 4.0 m wide.
Vigor: Medium.
Density: Medium.
Form: Upright to spreading.
Production: Precocious, produces regular good crops.

Growth type: Ramified.

Bearing: Annual bearing habit on spurs and one-year-old shoots.

Trunk:

*Size.*—Height 113.0 cm, diameter at soil 15.0 cm.

*Surface texture.*—Semirough to rough.

*Bark color.*—Greyed-orange RHS 165B.

*Lenticels.*—Length: 1.0 to 3.0 mm. Width: 1.0 to 2.0 mm. Color: Grey-brown RHS 199D. Density: Dense.

Branches:

*Diameter.*—Lower branches at the trunk are 5.0 cm.

*Surface texture.*—Semirough.

*Color.*—Greyed-orange RHS 177A.

*Form.*—Ramified.

*Average angle.*—70°.

*Bud arrangement.*—Flower buds on medium long spurs and one-year-old shoots.

*Lenticels.*—Length: 1.0 to 2.0 mm. Width: 1.0 to 2.0 mm. Shape: Round to oval. Density: Medium. Color: Grey-brown RHS 199D.

Leaves:

*Length.*—77.0 mm.

*Width.*—50.0 mm.

*Form.*—Oval.

*Texture.*—Smooth, glossy.

*Thickness.*—Medium to thick.

*Base.*—Slightly irregular.

*Apex.*—Short, mucronate.

*Margin.*—Crenate.

*Pubescence.*—Upper surface: Absent. Lower surface: Medium.

*Color.*—Young leaves: Upper surface: Yellow-green RHS 144A–B. Lower surface: Yellow-green RHS 144B. Mature leaves: Upper surface: Yellow-green RHS 147A. Lower surface: Yellow-green RHS 147C.

*Petiole.*—Shape: Straight to slightly bent. Length: 24.0 mm. Diameter: 1.8 mm. Color: Yellow-green RHS 147B, base of lower surface is slightly purple.

*Veins.*—Venation type: Medium dense with a 45° angle between the main veins. Color: Upper surface: Yellow-green RHS 147B. Lower surface: Yellow-green RHS 145C.

Flower buds:

*Pedicel.*—Length: 22.0 mm. Diameter: 1.2 to 1.5 mm. Color: Green RHS 143C.

*Bud.*—Length: 16 mm. Width: 13 mm. Color: Purple RHS 75A.

Flowers:

*Bloom timing.*—Early to medium. May 5, but varies depending on location and year; 1–2 days before 'Golden Delicious'.

*Blooming period.*—Medium.

*Pollination requirements.*—Normal, good pollinators, similar to crab apple 'Golden Hornet'.

*Number of flowers per cluster.*—5.

*Fragrance.*—Medium.

*Petals.*—Number: 5. Length: 20.0 mm. Width: 14 mm. Shape: Ovate. Aspect: Position mostly overlapping. Margin: Straight. Texture and appearance: Smooth, surface is wavy. Color: When opening: Upper surface: Red-purple RHS 74C to RHS 74D. Lower surface: Purple RHS 76B to RHS 76D. Fully opened: Upper surface: Predominantly white RHS 155D and slightly purple RHS 74D. Lower surface: White RHS 155D, with purple sections RHS 76C.

*Sepals.*—Shape: Acuminate. Margin: Straight. Length: 6.0 mm. Width: 3.0 mm at sepals union. Color: Upper surface: Yellow-green RHS 144B. Lower surface: Yellow-green RHS 144B.

*Stamens.*—Number (per flower): 19. Filament length: 5.0 to 10.0 mm.

*Anthers.*—Shape: Oval. Length: 2.0 mm. Color: Yellow RHS 10B.

*Pollen.*—Color: Yellow RHS 10B. Amount (generally): High.

*Pistils.*—Length: 15.0 mm.

*Style.*—Length: 10.0 mm. Color: Yellow-green RHS 145B.

*Stigma.*—Shape: Round. Color: Yellow-green RHS 150B.

Fruit:

*Maturity when described.*—Three months after picking.

*Date of picking.*—Oct. 6, 2003.

*Size.*—Axial diameter: 69.0 mm. Transverse diameter: 75.0 mm.

*Form.*—Globose, slightly conical.

*Cavity.*—Shape: Funnel-shaped. Depth: Medium, 13.0–15.0 mm. Breadth: Medium, 35 mm.

*Basin.*—Shape: Broadly funnel-shaped, slightly ribbed. Depth: Medium, 7.0–8.0 mm. Width: Broad, 35.0–40.0 mm.

*Calyx.*—Persistent, open.

Skin:

*Thickness.*—Medium.

*Texture.*—Smooth, without bloom and greasiness, russeting around cavity present.

*Tendency to crack.*—Absent.

*Color.*—Overcolor absent or blushed orange RHS 26A.

*Ground color.*—Yellow-orange RHS 15B.

Flesh:

*Aroma.*—Very good aromatic flavor, sweet, well balanced.

*Color.*—Yellow-orange RHS 16D.

*Texture.*—Intermediate.

*Eating quality.*—Very good.

Core:

*Bundle area.*—Core with seed cells oval on longitudinal section 18.0×22.0 mm.

*Bundle.*—Strands of conductive tissue on longitudinal section undistinguished, onion-shaped 28.0×28.0 mm.

*Capillary area.*—Eye basis medium deep, broad, 8.0×35–40.0 mm, slightly ribbed.

*Calyx tube.*—Short, open, broadly funnel shaped.

*Depth of tube to shoulder.*—13.0 mm.

*Styles.*—Present as dry residues.

*Stamens.*—Present as dry residues.

*Axillary cavity.*—Stalk cavity 13.0–15.0 mm deep, 35.0 mm broad.

*Seed cells.*—Wall: Medium thick. Depth: 10.0 mm. Breadth: 3.0–4.0 mm. Longitudinal section: Length of 18.0 mm.

Seeds:

*Number perfect.*—10.

*Number in one cell.*—Usually 2.

*Length.*—8.0 mm.

*Breadth.*—5.0 mm.

*Form.*—Usual apple seed form.

*Color.*—Greyed-orange RHS 175B–C.

Stem:

*Length.*—10.0 to 24.0 mm.

*Width.*—2.0–3.0 mm.

*Color.*—Yellow-green, almost RHS 153B.

Use: Late dessert variety for conventional and ecological fruit growing.

Shipping quality: Very good.

Keeping quality: Very good, approximately 6 months under natural storage.

Tree winter hardiness: No frost damage observed so far at the place of origin.

Bud winter hardiness: No frost damage observed so far at the place of origin.

Drought tolerance: Unknown.

Disease resistance: $V_f$ resistance against scab, tolerant to powdery mildew, no other diseases observed so far on trees untreated with fungicides.

I claim:

1. A new and distinct variety of *Malus Mill.* plant substantially as shown and described.

* * * * *

UNITED STATES PATENT AND TRADEMARK OFFICE

CERTIFICATE OF CORRECTION

PATENT NO. : PP15,963 P2
APPLICATION NO. : 10/862259
DATED : September 13, 2005
INVENTOR(S) : Tupy et al.

It is certified that error appears in the above-identified patent and that said Letters Patent is hereby corrected as shown below:

On the title page:

Column 1, Item (50), Latin Name: "*Malus Mill.*" should read -- *Malus Domestica* --

Column 2, Item (57) ABSTRACT, Line 1, "*Malus Mill.*" should read -- *Malus Domestica* --

Column 1, Botanical classification: "*Malus Mill.*" should read -- *Malus Domestica* --

Column 1, Line 7, "classified as *Malus Mill.*" should read -- classified as *Malus Domestica* --

Column 1, Line 32, "other *Malus Mill.* varieties" should read -- other *Malus Domestica* varieties --

Column 6, Claim 1, Line 1, "*Malus Mill.*" should read -- *Malus Domestica* --

Signed and Sealed this
Twenty-seventh Day of September, 2011

David J. Kappos

David J. Kappos
*Director of the United States Patent and Trademark Office*